US007338798B2

(12) United States Patent
Dennis et al.

(10) Patent No.: US 7,338,798 B2
(45) Date of Patent: Mar. 4, 2008

(54) SYSTEM AND METHOD FOR FORMING A CARDIAC MUSCLE CONSTRUCT

(75) Inventors: Robert G. Dennis, Ann Arbor, MI (US); Ravi K. Birla, Ann Arbor, MI (US); Marvin O. Boluyl, Ann Arbor, MI (US); Ellen M. Arruda, Ann Arbor, MI (US); Keith R. Baar, Ann Arbor, MI (US); Gregory H. Borschel, Ypsilanti, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 375 days.

(21) Appl. No.: 10/663,577

(22) Filed: Sep. 16, 2003

(65) Prior Publication Data

US 2004/0132184 A1 Jul. 8, 2004

Related U.S. Application Data

(60) Continuation-in-part of application No. 09/709,890, filed on Nov. 9, 2000, now Pat. No. 6,777,234, which is a division of application No. 09/153,721, filed on Sep. 15, 1998, now Pat. No. 6,207,451.

(51) Int. Cl.
*C12N 5/00* (2006.01)
(52) U.S. Cl. ..................................... 435/325
(58) Field of Classification Search ................. 435/325, 435/366; 424/93.7
See application file for complete search history.

(56) References Cited

U.S. PATENT DOCUMENTS

| | | | |
|---|---|---|---|
| 4,605,623 A | 8/1986 | Malette et al. | |
| 4,642,292 A | 2/1987 | Reid et al. | |
| 4,801,299 A | 1/1989 | Brendel et al. | |
| 4,940,853 A | 7/1990 | Vandenburgh | |
| 5,153,136 A | 10/1992 | Vandenburgh | |
| 5,443,950 A | 8/1995 | Naughton et al. | |
| 5,618,718 A | 4/1997 | Auger et al. | |
| 5,756,350 A | 5/1998 | Lee et al. | |
| 6,114,164 A | 9/2000 | Dennis et al. | |
| 6,207,451 B1 | 3/2001 | Dennis et al. | |
| 6,303,286 B1 | 10/2001 | Dennis et al. | |
| 6,448,076 B2 | 9/2002 | Dennis et al. | |
| 6,777,234 B1 * | 8/2004 | Dennis et al. | ............... 435/395 |
| 2001/0049138 A1 * | 12/2001 | Dennis et al. | ............... 435/325 |

OTHER PUBLICATIONS

Zimmermann et al, Three-DImensional Engineered Heart Tissue from Neonatal Rat Cardiac Myocytes, Biotechnology and Bioengineering, vol. 68, No. 1, p. 106-114, 2000.*
Shimizu, Tatsuya, Cardiac Tissue Engineering-Myocardial Tissue Construction using Biomaterials, 2000, Igaku no Ayumi, vol. 195, p. 203-204.*
Shimizu et al, Cell Sheet engineering for myocardial tissue reconstruction,2003,Biomaterials, vol. 24, p. 2309-2316.*

L.W. Stevenson et al., "The Impending Crisis Awaiting Cardiac Transplantation", Circulation, vol. 89, No. 1, Jan. 1994, pp. 450-457.
R.E. Akins et al., "Cardiac Organogenesis in vitro: Reestablishment of Three-Dimensional Tissue Architecture by Dissociated Neonatal Rat Ventricular Cells", Tissue Engineering, vol. 5, No. 2, 1999, pp. 103-118.
M. Muthuchamy et al., "Developmental Analysis of Tropomyosin Gene Expression in Embryonic Stem Cells and Mouse Embryos", Molecular and Cellular Biology, Jun. 1993, vol. 13, No. 6, pp. 3311-3323.
I. Harary and B. Farley, "In Vitro Studies On Single Beating Rat Heart Cells", Experimental Cell Research 29, 1963, pp. 451-465.
T. Eschenhagen et al., "Three-dimensional reconstitution of embryonic cardiomyocytes in a collagen matrix: a new heart muscle model system", The FASEB Journal, vol. 11, Jul. 1997, pp. 683-694.
L. Saggin et al., "Troponin T Switching in the Developing Rat Heart", The Journal of Biological Chemistry, vol. 263, No. 34, Dec. 15, 1988, pp. 18488-18492.
P. Anderson and A. Oakeley, "Immunological Identification of Five Troponin T Isoforms Reveals an Elaborate Maturational Troponin T Profile in Rabbit Myocardium", Circulation Research, vol. 65, No. 4, Oct. 1989, pp. 1087-1093.
L. Gao et al., "Differential Expression of TnI and TnT Isoforms in Rabbit Heart during the Perinatal Period and during Cardiovascular Stress", J. Mol. Cell. Cardiol. 27, 1995, pp. 541-550.
W. Zimmermann et al., "Cardiac Grafting of Engineered Heart Tissue in Syngenic Rats", Circulation Research, Sep. 24, 2002, pp. I-151-I-157.
W. Zimmermann et al., "Tissue Engineering of a Differentiated Cardiac Muscle Construct", Circulation Research, Feb. 8, 2002, pp. 223-230.
T. Kofidis et al., "A novel bioartificial myocardial tissue and its prospective use in cardiac surgery", European Journal of Cardiothoracic Surgery, 22, 2002, pp. 238-243.
A. Kadner et al., "Human Umbilical Cord Cells: A New Cell Source for Cardiovascular Tissue Engineering", Annals of Thoracic Surgery 74, 2002, pp. S1422-S1428.
R. Dennis and P. Kosnik, "Excitability and Isometric Contractile Properties of Mammalian Skeletal Muscle Constructs Engineered In Vitro", In Vitro Cell. Dev. Biol., May 2000, pp. 327-335.
R. Dennis et al., "Excitability And Contractility Of Skeletal Muscle Engineered From Primary Cultures And Cell Lines", Am. J. Physiol Cell Physiol, 2001, C288-C295.

(Continued)

*Primary Examiner*—Sandra E. Saucier
*Assistant Examiner*—Tiffany Gough
(74) *Attorney, Agent, or Firm*—Brooks Kushman P.C.

(57) ABSTRACT

A system and method for forming a cardiac muscle construct are provided, the system including a substrate and cardiac cells provided on the substrate in the absence of a scaffold. The cardiac cells are cultured in vitro under conditions to allow the cells to become confluent and detach from the substrate to form a three-dimensional cardiac muscle construct.

35 Claims, 6 Drawing Sheets

OTHER PUBLICATIONS

R. Carrier et al., "Cardiac Tissue Engineering: Cell Seeding, Cultivation Parameters, and Tissue Construct Characterization", Biotechnology and Bioengineering, vol. 64, No. 5, Sep. 5, 1999, pp. 580-589.

R. Akins, "Can Tissue Engineering Mend Broken Hearts?", Circulation Research, Feb. 8, 2002, pp. 120-122.

P. Akhyari et al., "Mechanical Stretch Regimen Enhances the Formation of Bioengineered Autologous Cardiac Muscle Grafts", Circulation, Sep. 24, 2002, pp. I-137-I-142.

Vandenburgh et al., Skeletal Muscle Growth is Stimulated by Intermittent Stretch-Relaxation in Tissue Culture, American Psych. Society, 1989, pp. C674-682.

Vandenburgh, A Computerized Mechanical Cell Stimulator for Tissue Culture Effects on Skeletal Muscle Organogenesis, In Vitro Cellular & Developmental Biology, vol. 24, No. 7, Jul. 1988, pp. 609-619.

Vandenburgh et al., Longitudinal Growth of Skeletal Myotubes in Vitro in a New Horizontal Mechanical Cell Stimulator, In Vitro Cell Dev. Bio., vol. 25, No. 7, Jul. 1989, pp. 607-616.

Vandenburgh et al., Computer-Aided Mechanogenesis of Skeletal Muscle Organs from Single Cells In Vitro, The FASEB Journal, vol. 5, Oct. 1991, pp. 2860-2867.

Vandenburgh et al., Tissue-Engineered Skeletal Muscle Organoids for Reversible Gene Therapy, Humane Gene Therapy, Nov. 1996, pp. 2195-2200.

Shansky et al., Letter to the Editor: A Simplified Method for Tissue Engineering Skeletal Muscle Organoids In Vitro, In Vitro Cell. Dev. Biol., Oct. 1997, pp. 659-661.

T. Shimizu et al., "Two-Dimensional Manipulation of Cardiac Myocyte Sheets Utilizing Temperature-Responsive Culture Dishes Augments the Pulsatile Amplitude", Tissue Engineering, vol. 7, No. 2, 2001, pp. 141-151.

T. Shimizu et al., "Electrically communicating three-dimensional cardiac tissue mimic fabricated by layered cultured cardiomyocyte sheets", Journal of Biomedical Materials Research 60, pp. 110-117, 2002.

T. Sakai et al., "The Fate Of A Tissue-Engineered Cardiac Graft In The Right Ventricular Outflow Tract Of The Rat", The Journal of Thoracic and Cardiovascular Surgery, vol. 121, No. 5, May 2001, pp. 932-942.

M. Papadaki et al., "Tissue Engineered Of Functional Cardiac Muscle: Molecular, Structural, and Electrophysiological Studies", Am. J. Physiol Heart Circ. Physiol 280, 2001, pp. H168-H178.

T. McDevitt et al., "In vitro generation of differentiated cardiac myofibers on micropatterned laminin surfaces", Journal of Biomedicial Materials Research 60, 2002, pp. 472-479.

W. Liu et al., "Developmental changes of $Ca^{2-}$ handling in mouse ventricular cells from early embryo to adulthood", Life Sciences 71, 2002, pp. 1279-1292.

J. Leor et al., "Bioengineered Cardiac Grafts, A New Approach To Repair The Infracted Myocardium?", Circulation, Nov. 7, 2000, pp. III-56-III-61.

P. Kosnik et al., "Functional Development of Engineered Skeletal Muscle From Adult And Neonatal Rats", Tissue Engineering, vol. 7, Nov. 5, 2001, pp. 573-584.

T. Kofidis et al., "In vitro engineering of heart muscle: Artificial Myocardial tissue", The Journal of Thoracic and Cardiovascular Surgery, vol. 124, No. 1, pp. 63-69, 2002.

\* cited by examiner

β-Tm →
α-Tm →

SYSTEM AND METHOD FOR FORMING A CARDIAC MUSCLE CONSTRUCT

CROSS-REFERENCE TO RELATED APPLICATIONS

This application is a continuation-in-part of U.S. application Ser. No. 09/709,890 filed Nov. 9, 2000, now U.S. Pat. No. 6,777,234, which is a divisional of U.S. application Ser. No. 09/153,721 filed Sep. 15, 1998, now U.S. Pat. No. 6,207,451.

STATEMENT REGARDING FEDERALLY SPONSORED RESEARCH OR DEVELOPMENT

The invention was made with Government support under Contract No. N66001-02-C-8034 from DARPA (Contracting Agent: SPAWAR).

BACKGROUND OF THE INVENTION

1. Field of the Invention

This invention relates to the field of tissue engineering, and more particularly to a system and method for producing a cardiac muscle construct in vitro.

2. Background Art

At present, three-dimensional tissues are capable of being produced in vitro using various types of cells. For example, U.S. Pat. No. 5,443,950 issued to Naughton et al. describes three-dimensional cultures for bone marrow, skin, liver, vascular, and pancreatic tissues which are grown within synthetic matrices. In these tissues as well as others, investigators have been successful in proliferating cells and tissues in vitro such that the resulting three-dimensional tissues, termed "organoids" or "constructs", display many of the characteristics of their in vivo counterparts. These constructs have a variety of foreseeable applications, ranging from transplantation in vivo to functional and pharmacological testing in vitro.

In terms of muscle tissue, in vitro constructs of smooth muscle, skeletal muscle, and cardiac muscle have each been formulated. For cardiac muscle, U.S. Pat. No. 4,605,623 issued to Malette et al., for example, describes a method for cultivating the three-dimensional growth of cardiac myocytes within a chitosan scaffold material. Although this and other scaffold-based cardiac tissue constructs have been reported (see Atkins et al., *Tissue Eng* 5, 103-18, April 1999; Akhyari et al., *Circulation* 106, I137-42, September 2002; Bursac et al., *Am J Physiol* 277, H433-44, August 1999; Carrier et al., *Biotechnol Bioeng* 64, 580-9, September 1999; Fink et al., *Faseb J* 14, 669-79, April 2000; Kofidis et al., *J Thorac Cardiovasc Surg* 124, 63-9, July 2002; Kofidis et al., *Eur J Cardiothorac Surg* 22, 238-43, August 2002; Leor et al., *Circulation* 102, I1156-61, November 2000; Zimmerman et al., *Circ Res* 90, 223-30, February 2002; Zimmerman et al., *Circulation* 106, I151-7, September 2002; Taylor et al., *J Heart Valve Dis* 11, 298-307, May 2002; Papadaki et al., *Am J Physiol Heart Circ Physiol* 280, H168-78, January 2001; McDevitt et al., *J Biomed Mater Res* 60, 472-9, June 2002), the creation of a self-organizing contractile cardiac muscle construct in culture has proven elusive. There are many reasons for this, including the fact that cardiac myocytes are post-mitotic such that they no longer undergo cell division to produce greater numbers of cells, making it difficult or impossible to amplify cardiac myocytes in culture.

SUMMARY OF THE INVENTION

Therefore, it is an object according to the present invention to provide a system and method for producing a cardiac muscle construct in vitro.

It is a further object according to the present invention to provide a system and method for inducing cardiac myocytes to self-assemble into a three-dimensional cardiac muscle construct.

It is a still further object according to the present invention to provide a system and method for producing a cardiac muscle construct that self-organizes without the need for exogeneous scaffolding.

Accordingly, a system for forming a cardiac muscle construct is provided which includes a substrate and cardiac cells provided on the substrate in the absence of a scaffold. The cardiac cells are cultured in vitro under conditions to allow the cells to become confluent and detach from the substrate to form a three-dimensional cardiac muscle construct.

The cardiac cells self-organize to form the three-dimensional cardiac muscle construct, and may include cardiac myocytes as well as fibroblasts. The resulting cardiac muscle construct is spontaneously contractile, is responsive to electrical stimuli, is responsive to chemical stimuli, and is resistant to fatigue. The cardiac muscle construct is substantially cylindrical. In an alternative embodiment, skeletal muscle cells can be cultured in combination with the cardiac cells.

In a preferred embodiment, the system further includes at least two anchors secured to the substrate in spaced relationship with at least some of the cardiac cells in contact with and attachable to the anchors. The anchors can include silk suture segments coated with cell adhesion molecules, such as laminin. The substrate may also be coated with cell adhesion molecules. Preferably, the cell adhesion molecules include laminin at a concentration of laminin about 0.4 to 2.0 $\mu g/cm^2$.

Correspondingly, a method according to the present invention for forming a cardiac muscle construct includes providing a scaffold-free substrate, providing cardiac cells on the substrate, and culturing the cardiac cells in vitro under conditions to allow the cells to become confluent and detach from the substrate to form a three-dimensional cardiac muscle construct.

In a preferred embodiment, the cardiac cells include cardiac myocytes and may also include fibroblasts. In addition, skeletal muscle cells could be cultured with the cardiac cells. The method can also include eliciting a response of the cardiac muscle construct to electrical stimuli and to chemical stimuli. Furthermore, the method can include measuring a functional property of the cardiac muscle construct and using the measured property as feedback to control the formation of the cardiac muscle construct. Still further, the method according to the present invention may include implanting the cardiac muscle construct in a suitable recipient.

According to a preferred embodiment of the present invention, the method includes securing at least two anchors to the substrate in spaced relationship with at least some of the cardiac cells in contact with the and attachable to the anchors. The anchors can include silk suture segments coated with cell adhesion molecules, preferably laminin. Additionally, the method preferably further includes coating the substrate with cell adhesion molecules, including laminin. The preferred concentration of laminin on the substrate is about 0.4 to 2.0 $\mu g/cm^2$.

In further accordance with the present invention, a cardiac muscle construct is provided which includes cardiac myocytes provided on a scaffold-free substrate. The cardiac myocytes are cultured in vitro under conditions to allow the myocytes to self-organize and become a confluent monolayer, where the monolayer detaches from the substrate to form a three-dimensional cardiac muscle construct.

The cardiac muscle construct may include fibroblasts provided in combination with the cardiac myocytes. The construct is spontaneously contractile, is responsive to electrical stimuli, is responsive to chemical stimuli, and is resistant to fatigue. The construct is substantially cylindrical in shape, and includes both adherens junctions and gap junctions formed between the cardiac myocytes.

The above objects and other objects, features, and advantages of the present invention are readily apparent from the following detailed description of the best mode for carrying out the invention when taken in connection with the accompanying drawings.

DETAILED DESCRIPTION OF THE PREFERRED EMBODIMENT(S)

Figure 1A:
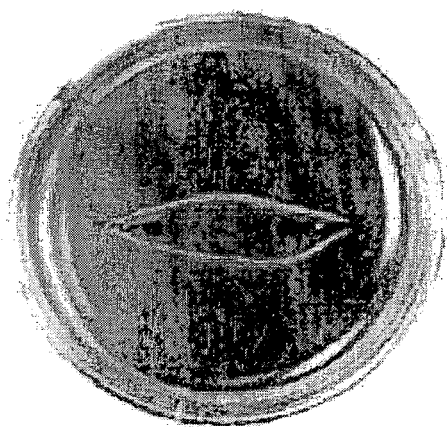
FIGS. 1A-1D are photographs depicting the self-organization of a cardiac muscle construct in culture according to the present invention, wherein the photographs were taken at 14 days (FIG. 1A), 15 days (FIG. 1B), and 21 days (FIG. 1C) after plating, and after connection to the experimental apparatus for functional measurements (FIG. 1D)

The present invention provides a system and method for culturing cardiac cells in such a way as to promote the self-organization of a three-dimensional, contractile cardiac muscle construct in culture. The contractile constructs do not employ an artificial scaffold in their contractile region; rather, the construct self-organizes from a cohesive monolayer of cardiac myocytes and fibroblasts. These constructs are designated herein as "cardioids," as they are similar to cardiac muscle in terms of cell-to-cell connectivity and contractility. A method for the culture of primary skeletal muscle myogenic precursor cells is disclosed in commonly assigned U.S. Pat. No. 6,207,451 which is incorporated by reference herein. According to the present invention, this method has been optimized to promote the self-organization of cardiac cells in vitro.

By way of example, the system and method for producing the cardioids of the present invention are described with reference to the use of cardiac tissue originating from rats. However, the system and method of the present invention are not intended to be limited to one particular cell origin or age, cardioid shape, time frame, component concentration, or culture condition. For example, it is fully contemplated that cardiac tissue from any mammal, including human beings, could be similarly utilized according to the system and method described herein. One skilled in the art can readily appreciate that various modifications can be made to the system and method described herein without departing from the scope of the invention disclosed.

As is apparent to those skilled in the art, the culture of cells as described below must be carried out in accordance with commonly practiced cell culture techniques. For example, all materials and media which will be placed in contact with living cells must be appropriately sterilized and handled. In addition, the cells and cardioids must be maintained in an otherwise aseptic environment. Of course, it is understood that all reagent measurements and submersion times described herein are approximate, and can be varied slightly without affecting the resulting method.

In the description and data that follow, cardiac myocytes were isolated from the hearts of neonatal (1-3 day old) F344 rats. According to the method of the present invention, the hearts are preferably minced into small pieces and then cardiac cells are dissociated by placement in a 0.25% trypsin-EDTA solution containing 200 units/ml type I collagenase, wherein the collagenase is pre-screened to ensure the optimal recovery of cardiac myocytes. The solution is placed in a reciprocal shaking bath at 37° C. for approximately 6 hours to facilitate breakdown of the extracellular matrix. After the tissue is dissociated, the cells are pelleted by centrifugation at 100 g for approximately 15 minutes and the supernatant is then removed by aspiration. The cells are resuspended with plating medium (335 ml DMEM, 85 ml M199, 25 ml fetal bovine serum (FBS), 50 ml horse serum, 100 units/ml antibiotic-antimycotic). Within this suspension of cardiac cells will likely be fibroblasts in addition to the cardiac myocytes. There is not a need to eliminate the fibroblasts, and in fact the inclusion of fibroblasts may facilitate the generation of extracellular matrix components which provide mechanical support for the tissue.

A scaffold-free substrate on which to form the cardioids of the present invention is preferably created by coating 35 mm culture dishes with polydimethylsiloxane (PDMS) or another elastomeric polymer having similar non-porous, hydrophobic properties. After curing for ~2 weeks, the dishes are rinsed with Dulbecco's phosphate-buffered saline (DPBS) or another suitable balanced salt solution. The adhesion and migration of cells on the hydrophobic PDMS substrate material is promoted using the extracellular matrix protein laminin, where approximately 0.6 µg/cm² natural mouse laminin is applied to the substrate as a solution in DPBS. The DPBS is allowed to evaporate overnight in a biological safety cabinet, leaving a layer of laminin-coated PDMS.

The laminin concentration on the substrate is used to control the time of cell monolayer delamination for the formation of the cardioids of the present invention. In particular, the laminin disappears from the substrate within a couple of weeks, which facilitates the detachment process to allow cardioid formation. The density of laminin on the PDMS substrate dictates not only cell survival, but also the rate at which the cells reform into a three-dimensional structure (see Dennis and Kosnik, *In Vitro Cell Dev Biol Anim* 36, 327-35, May 2000; Kosnik et al., *Tissue Eng* 7, 573-84, October 2001). Higher laminin concentrations result in more rapid formation of dense monolayers of confluent cells, but also delay the delamination of the monolayer. The optimal concentration of laminin for use in the present invention appears to be in the range of about 0.4 $\mu g/cm^2$ to 2.0 $\mu g/cm^2$. Of course, a cell adhesion protein other than laminin could alternatively be used.

According to a preferred embodiment of the invention, silk suture segments coated with cell adhesion molecules are utilized as anchors within the culture dishes. The anchors function as constraints or guides around which the delaminating cell layer forms the cardioid, and are permeable to allow the ingrowth of tissue. Preferably, the cell adhesion molecules are extracellular matrix attachment molecules, most preferably laminin. The anchors are produced by cutting silk suture, preferably size 0, to a convenient length. Lengths of 6 to 8 mm are easily pinned in place, but the length can be varied without limit as dictated by the specific circumstances. The segments of suture are dipped in a solution of 50 µg/ml laminin, preferably natural mouse laminin (Gibco), in DPBS with care taken to thoroughly wet the suture. The suture segments are then allowed to dry before use. Advantageously, attachment of the cardiac cells to the anchors does not restrict the ability to perform subsequent functional measurements on the cardioids.

As described in U.S. Pat. No. 6,207,451 incorporated herein by reference, the anchors can alternatively be produced from small acellularized fragments of muscle, wherein the acellularized fragments have cell adhesion molecules associated therewith. Preferably, the fragments contain extracellular matrix attachment molecules, such as laminin, collagen, or pronectin.

The anchors are preferably pinned approximately 10 to 20 mm apart in the prepared culture dish with stainless steel minutien pins, and the dishes are filled with enough plating medium to cover the top of the sutures. The dishes are sterilized via ultraviolet irradiation in a biological safety cabinet for approximately 90 minutes, and then placed in an incubator (5% $CO_2$, 37° C.) for 5-8 days prior to seeding with cardiac cells. It is believed that during incubation the proteins in FBS adhere to the substrate and anchors, thereby enhancing cell adhesion. Although two anchors are used to create the cardioid shape depicted herein, it is understood that more anchors may be used to form any desired cardioid size or shape.

After incubation, the plating medium is aspirated and cardiac cells are plated at high density, preferably approximately $2-4 \times 10^6$ cells/dish, due to the non-proliferative nature of cardiac myocytes medium (365 ml DMEM, 100 ml M199, 35 ml FBS, 100 units/ml antibiotic-antimycotic) is substituted for plating medium to induce cardioid formation. The culture medium is changed every ~2-3 days and the culture dishes are maintained in an incubator (37° C., 5% $CO_2$) until the cardioids are used for testing.

Figure 1C:
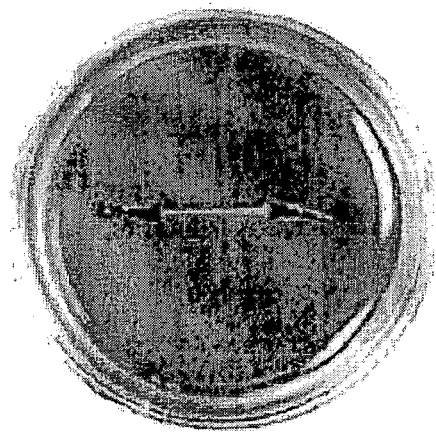
Figure 1B:
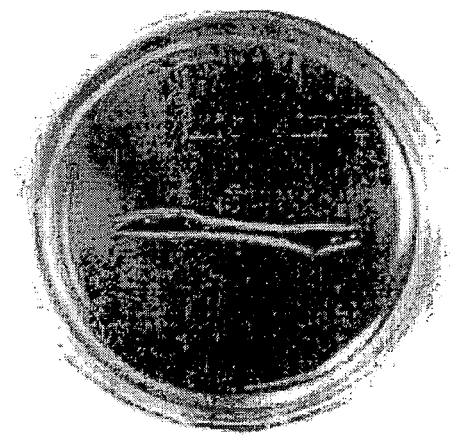

FIGS. 1A-1C depict the progressive delamination of the two-dimensional cell layer and gradual self-organization into the three-dimensional cardioid according to the present invention. A confluent monolayer is observed within 48 hours of plating cardiac cells and within one week the monolayer appears to contract as a syncytium. After about 2 weeks, the cell monolayer begins to detach from the PDMS substrate, beginning with a peripheral delamination of the edges of the tissue (FIG. 1A). The rate of delamination is dependent on many factors including the plating density, the adhesion of the cells to the substrate, the persistence of laminin over time, the passive tension generated by the cells, and the active contractile tension produced by the cardiac myocytes. Once the cell monolayer begins to detach from the substrate, the delamination process is generally quite progressive (FIG. 1B), and generally accelerates after each subsequent feeding. Typically, with each active contraction, the boundary of delamination moves radially inward. This in turn results in additional mechanical strain on the cells that are still attached to the substrate in proximity to the delamination boundary, progressively releasing the remaining cells from the substrate below while remaining attached to the suture anchors at each end.

The peak rate of delamination generally occurs at the point at which the delamination front has progressed ~50% of the radial distance from the outer circumference of the culture substrate, where the monolayer may delaminate as much as 50 µm during each active contraction. At the peak rate, the process of self-organization of the monolayer into a cylindrical, three-dimensional structure is visible to the naked eye. At about 3 weeks after plating, the cell monolayer completely detaches from the PDMS substrate, while remaining attached at both anchor points, forming a 3-dimensional, self-organized cardiac muscle construct suspended under tension between the anchors (FIG. 1C). No external influence is necessary for the cell layer to detach from the substrate as the system and method according to the present invention are optimized to promote delamination of the confluent monolayer.

The self-assembling process of the cardioids of the present invention is highly repeatable. The cardioids can be maintained in culture for approximately 60 days, wherein the time depends upon such conditions as the density at which the cells are plated, the anchor material and spacing, the frequency of feeding, and the type and density of the substrate cell adhesion molecules, such as laminin. Preferably, the cardioids are maintained in culture by feeding with culture medium every 2-4 days. There should be no limitations on the length or diameter of the cardioids that can be created.

With reference to commonly assigned U.S. Pat. Nos. 6,114,164 and 6,303,286, both incorporated by reference herein, the formation of the cardioids of the present invention could be guided by measuring a functional property of the construct, such as a passive or active force, and subsequently using the measured property in a feedback control loop.

For morphological analysis, the resulting cardioids of the present invention were fixed for 4 hours at 4° C. in a 0.1 M sodium cacodylate buffer solution pH=7.4 (Electron Microscopy Sciences, Fort Washington, Pa., 15950) containing 3% formaldehyde/glutaraldehyde. After fixation, the samples were rinsed with cacodylate buffer (pH=7.4) containing 7.5% sucrose, post-fixed in 1% osmium tetroxide, dehydrated, and embedded in EPON (Ted Pella Inc., Redding, Calif., Eponate 12 resin) and sectioned into 50 nm longitudinal strips. The strips were mounted on uncoated copper grids and stained with aqueous uranyl acetate and lead citrate. The ultrastructure of the cardioids was investigated using a transmission electron microscope at 60 kV.

Figure 2A:
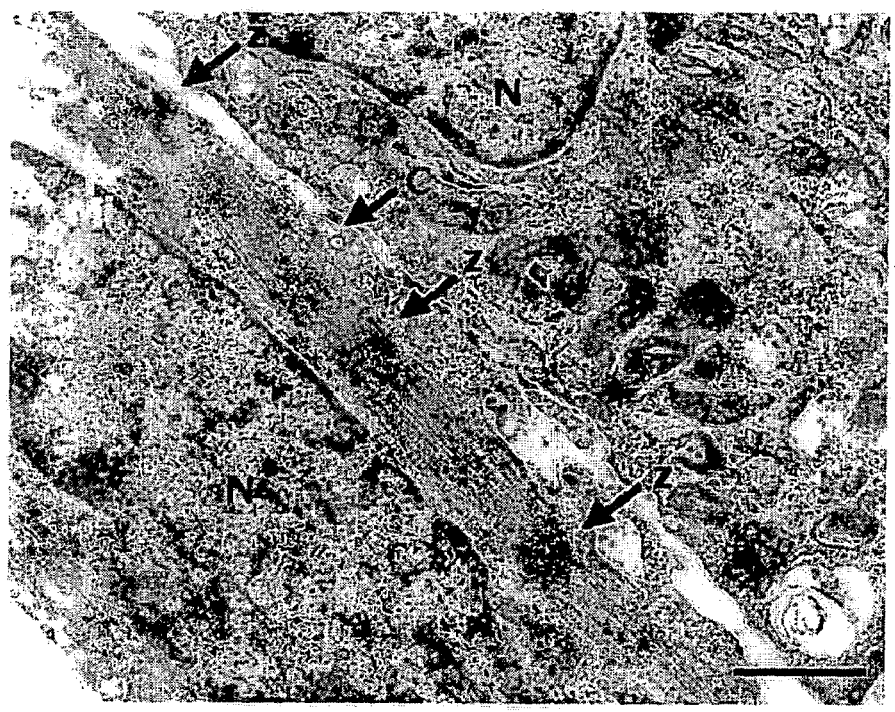
FIGS. 2A and 2B are electron micrographs of longitudinal sections of representative cardiac muscle constructs according to the present invention, the structures shown including z lines (Z), mitochondria (Mi), nuclei (N), collagen fibers (C), adherens junctions (AJ), and gap junctions (GJ), wherein the bar in each figure is 1 µm.
Figure 2B:
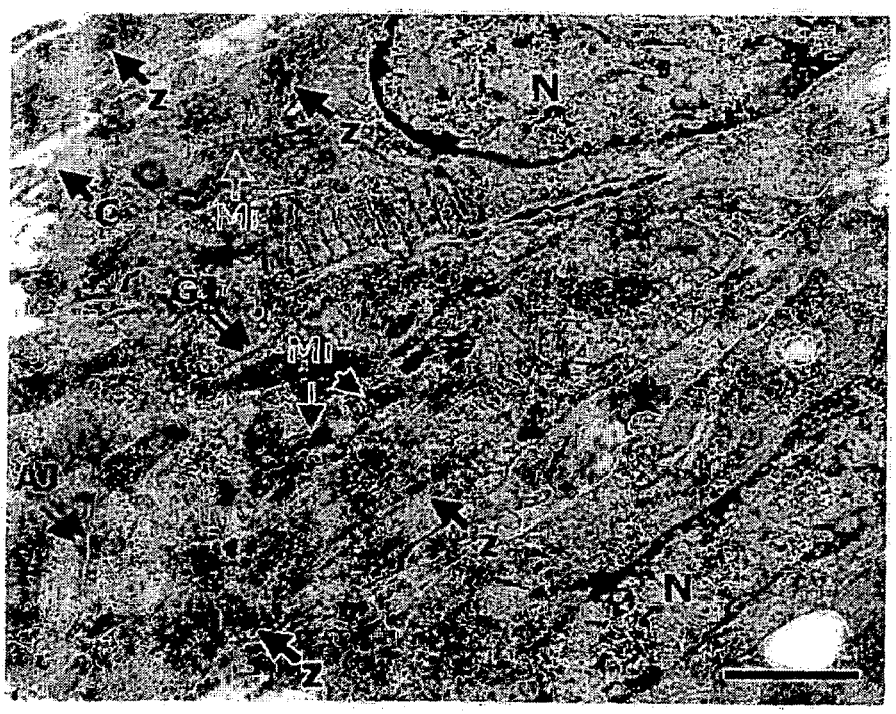

FIGS. 2A and 2B are electron micrographs of longitudinal sections of a representative fully-formed cardioid, such as that shown in FIG. 1C. As one skilled in the art will readily appreciate, the cardioid sections shown in FIGS. 2A and 2B clearly display a morphology indicative of in vivo cardiac muscle tissue, resembling a papillary muscle. The early stages of sarcomere development in the cardioid of the present invention are quite evident, with organized contractile units having a preponderance of short sarcomeres (~0.9 μm average) connected by primitive z lines (Z). The normal range for sarcomere lengths in the rat heart is 2.0 to 2.4 μm, such that it appears that sarcomeres within the cardioid are shortened during the process of delamination and reorganization of the cell monolayer. As in heart tissue, areas rich in mitochondria (Mi) flank the regions of contractile machinery. Each cell has a single prominent nucleus (N) and is surrounded by regions of connective tissue with parallel collagen fibers (C) between the cells. Between the cardiac myocytes are electron dense regions indicating that adherens junctions (AJ) have formed between the cardiac myocytes in series. These are important structures as they serve as a mechanical link between the cardiac myocytes, holding the cells tightly together as they contract. In addition, a large number of gap junctions (GJ) are evident, particularly on the lateral surfaces of the cardiac myocytes. These structures serve as a chemical linkage between the cells and may be important in electrical coupling of the cardiac myocytes.

Figure 1D:
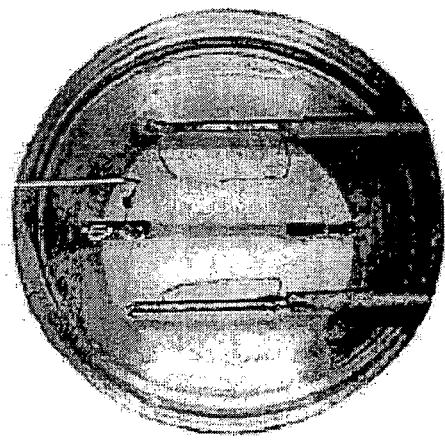
Figure 3A:
FIGS. 3A-C are graphs depicting the isometric force (top traces) resulting from electrical stimulation (bottom traces) of the cardiac muscle constructs according to the present invention for a single 10 V electrical pulse of 10 msec duration (FIG. 3A), a series of nine 10 V stimulation pulses applied at a frequency of 1 Hz (FIG. 3B), and a series of 10 V stimulation pulses applied at a frequency of 100 Hz (FIG. 3C)
Figure 3B:
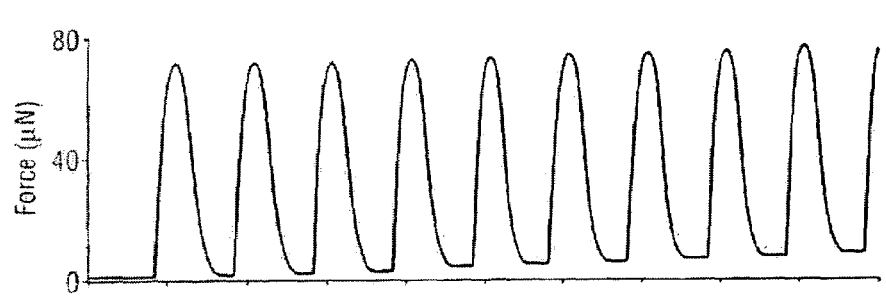
Figure 3C:
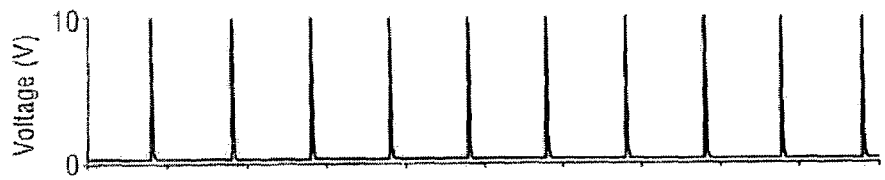
Figure 3C:
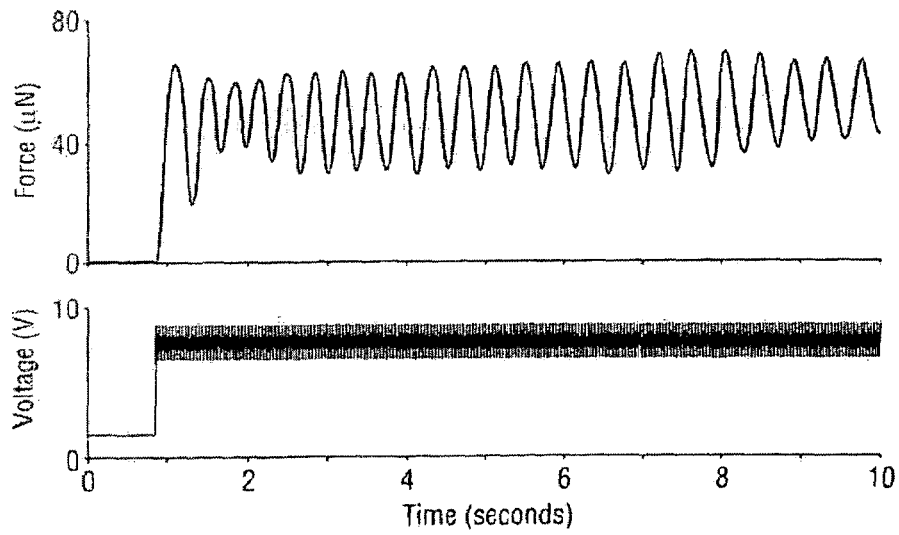

Contractile properties of the cardioids are easily evaluated by freeing one of the anchors from the substrate, affixing a force transducer, adjusting the length of the specimen, applying electrical stimulus pulses between parallel platinum wire electrodes (FIG. 1D) to excite the cardioid with a transverse electric field, and measuring and recording the forces elicited with the force transducer and a standard analog-to-digital data acquisition system. The isometric contractility of the cardioids of the present invention is illustrated in FIG. 3, wherein measurements were undertaken shortly after the self-organization of the cardioids into three-dimensional structures was complete. In all graphs, the top traces depict force (μN) as a function of time, while the bottom traces show the electrical pulses used to stimulate the cardioids. The newly formed cardioids exhibited spontaneous contractility and were electrically excitable between the electrodes. The different stimulation conditions shown are the application of a single 10 msec electrical pulse (10 V) (FIG. 3A), the application of a series of nine 10 V stimulation pulses at a frequency of 1 Hz (FIG. 3B), and the application of a series of 10 V stimulation pulses at a frequency of 100 Hz (FIG. 3C).

As illustrated in FIG. 3, contraction of the cardioids followed the all-or-none principle more common to skeletal muscle. As is true for excised cardiac muscle, the peak force generated by a single twitch (FIG. 3A) was equivalent to the peak force generated by a series of twitches in rapid succession (FIG. 3C). The cardioids could be entrained to contract with a "pacemaker" set to 1 Hz (FIG. 3B) for an indefinite period without detectable fatigue. By comparison, similar skeletal muscle constructs (disclosed in U.S. Pat. No. 6,207,451) require 30 to 120 seconds between peak twitches to once again be able to produce and equivalent peak twitch force (see Zimmerman et al., *Circulation* 106, I151-7, September 2002). On average, the peak active force of the cardioids tested was 70 μN, with an average baseline force of 260 μN. Normalizing by the total cross-sectional area of the smallest diameter of each cardioid, the resulting average specific force (stress) generation was 1.426 kPa, a ten-fold increase in force production over scaffold-based muscle systems. The resting force is high relative to the active force produced by the cardioids, which may be due to the presence of fibroblasts in the cardioids and the extracellular matrix that they generate (see Kosnik et al., *Tissue Eng* 7, 573-84, October 2001).

Figure 4:
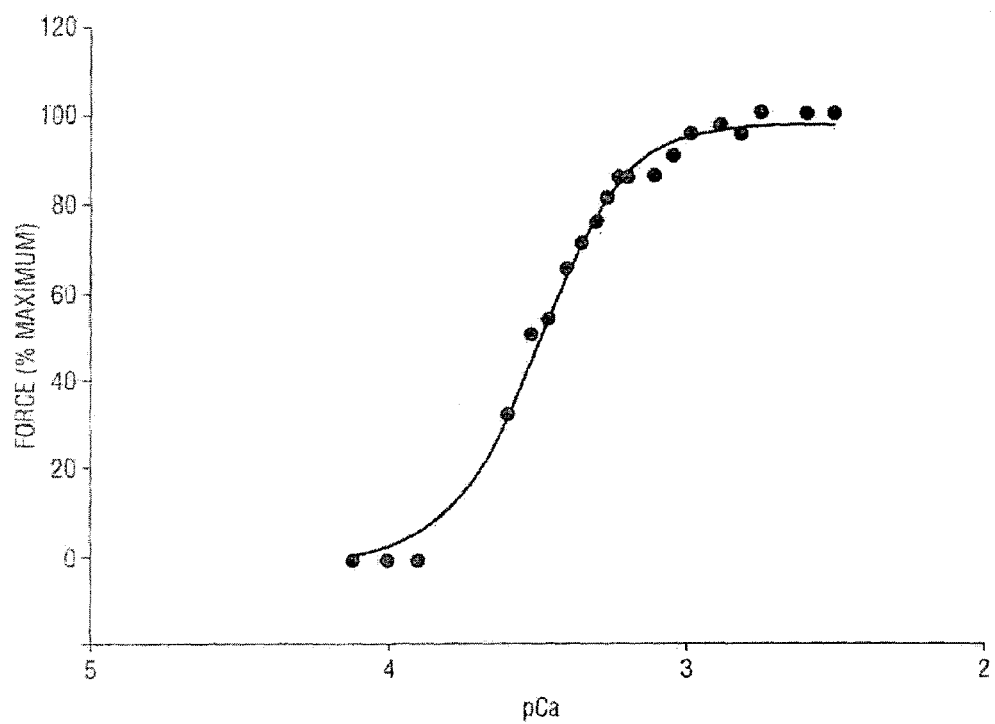
FIG. 4 is a graph of the percentage of maximal force as a function of calcium concentration (pCa) for the cardiac muscle constructs of the present invention.
Figure 5A:
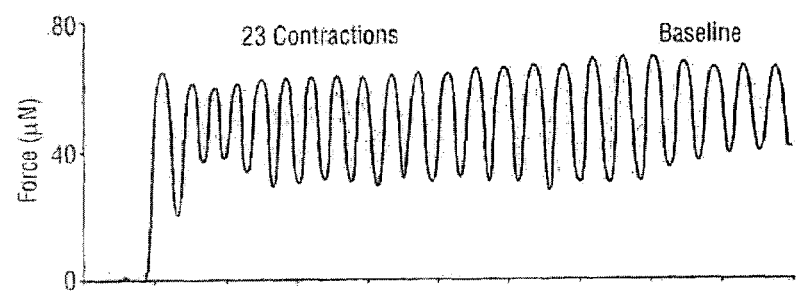
FIGS. 5A-E are graphs depicting the force response of the cardiac muscle constructs of the present invention to electrical stimulation of 10V pulses at a frequency of 100 Hz (FIG. 5E) in the absence of epinephrine (FIG. 5A), with 0.2 µg/ml of epinephrine (FIG. 5B), with 1.2 µg/ml epinephrine (FIG. 5C), and upon removal of the epinephrine from the culture media (FIG. 5D)
Figure 5B:
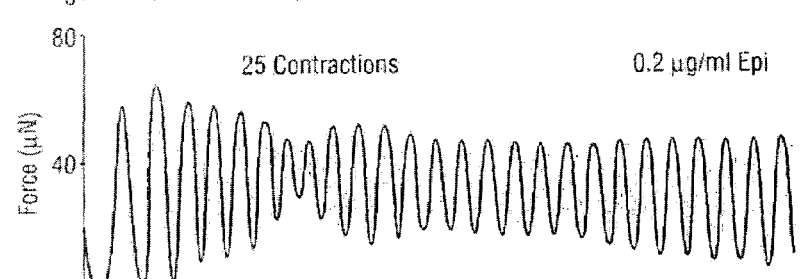
Figure 5C:
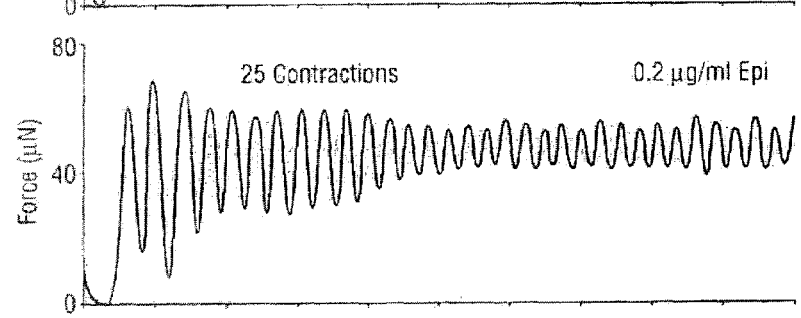
Figure 5D:
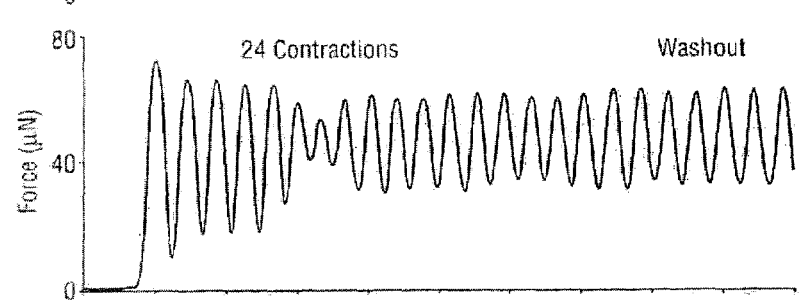
Figure 5E:
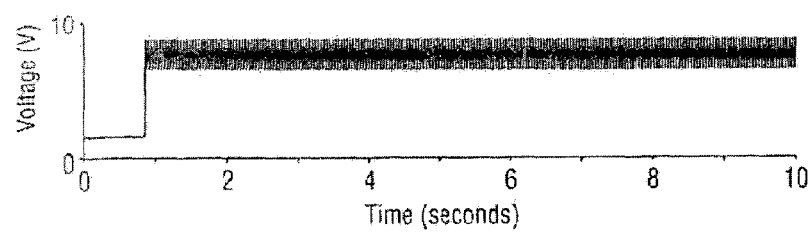

Turning now to FIG. 4, the effect of calcium concentration on the cardioids of the present invention was also investigated. Cardioids attached to a force transducer were electrically stimulated with a 10V pulse of 10 msec duration in media containing 0 to 0.01 M calcium. Twitch force was recorded and the percent maximal force was plotted as a function of pCa. At a given calcium concentration in the media, both spontaneous and induced contractions resulted in peak force production. However, as shown in FIG. 4, varying the calcium concentration modulated peak contractile force. The ability of cardioids to increase force production in response to increasing calcium suggests that they behave like cardiac muscle in their dependence on extracellular calcium for contraction.

To test the contractile response of cardioids of the present invention to cardioactive drugs, cardioids were stimulated in the presence of epinephrine. Epinephrine produces both inotropic and chronotropic effects on cardiac tissue. The chronotropic effect is due to the phosphorylation of both the calcium reuptake inhibitor phospholamban and troponin I. The phosphorylation of troponin I decreases myofilament calcium sensitivity thereby increasing the rate of relaxation, while the phosphorylation of phospholamban decreases its affinity for the sarco-endoplasmic reticulum calcium ATPase (SERCA). The release of phospholamban from SERCA increases the reuptake of calcium into the sarcoplasmic reticulum (SR). The greater calcium reuptake into the SR not only decreases the half-relaxation rate, but also increases inotropy due to the greater calcium store in the SR for release on subsequent contractions. Since the cardioids exhibited all-or-none contractions, an increase in inotropy was not expected. However, if the cardioids are able to respond to β-adrenergic stimuli, an increase in the rate of relaxation or chronotropic effects should be observed.

As shown in FIG. 5, two-day-old cardioids were electrically stimulated at 100 Hz for 9 seconds with increasing amounts of epinephrine and the force response was measured. A trace of the 10V stimulation pulses representing the voltage applied to the cardioids is shown in FIG. 5F, wherein the 800 ms delay in the onset of stimulation allows for the measurement of spontaneous contractions. FIG. 5A illustrates the isometric contractility of cardioids in the absence of epinephrine, where it can be noted that the stimulation does not produce a fused tetanus as it would for skeletal muscle constructs (see Dennis and Kosnik, *In Vitro Cell Dev Biol Anim* 36, 327-35, May 2000), but instead produces 23 separate contractions as a basal response. Treatment of the cardioids with 0.2 μg/ml epinephrine increased the number of contractions to 25 with greater relaxation between contractions, where a spontaneous contraction occurred prior to stimulation (FIG. 5B). The peak dose for the epinephrine effect on the cardioids was 1.2 μg/ml, which produced 32 contractions (FIG. 5C). To ensure that this effect was due to the presence of epinephrine, the epinephrine was washed out and fresh media was added, restoring the basal number of contractions (FIG. 5D). These data indicate that the cardioids of the present invention are not damaged or permanently altered by the addition of large concentrations of epinephrine, and that an accurate dose-response curve may be generated.

During the epinephrine experiments, the cardioids occasionally produced spontaneous contractions that would not respond to low level external electrical stimulation. The force produced by this type of spontaneous contraction was lower than normal, and was characterized by less well-synchronized contractions of the individual cardiac myocytes. This behavior is strikingly similar to fibrillation in cardiac muscle, which is a behavior that only occurs at the tissue level. Fibrillation arises from multiple action potential wavelets traveling in different directions that reenter a previously excited region of the cardiac muscle tissue. Thus, the observation of the phenomenon would not be possible if the cardioids were simply a collection of independent cells, since fibrillation requires the direct electrical coupling of many cells. As occurs in vivo, the cardioids could only be returned to normal contractile function by applying a greater voltage to the field.

Figure 6A:
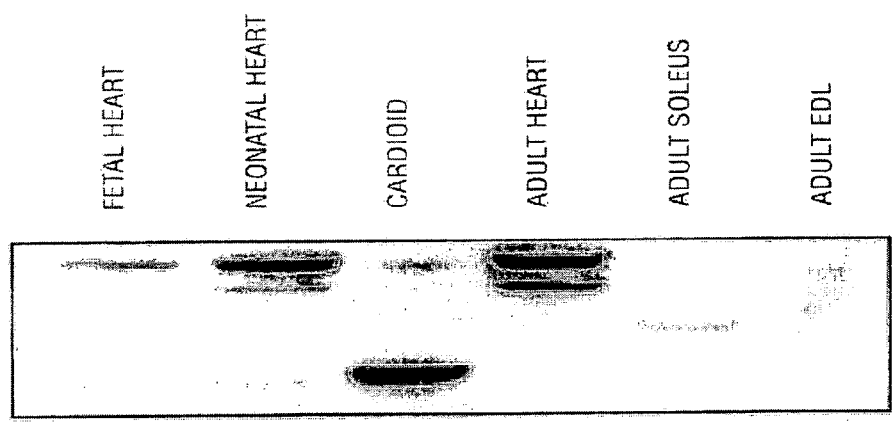
FIGS. 6A-C are western blots of fetal heart, neonatal heart, cardiac muscle constructs of the present invention, adult heart, slow skeletal muscle (adult soleus), and fast skeletal muscle (adult extensor digitorum longus—EDL) for goat polyclonal antibody directed against cardiac troponin T (cTnT) (FIG. 6A), mouse monoclonal antibody directed against the a and p forms of tropomyosin (Tm) (FIG. 6B), and goat polyclonal antibody directed at SERCA (FIG. 6C).
Figure 6B:
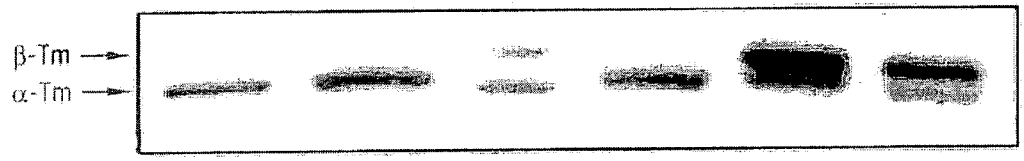
Figure 6C:

To determine the developmental state of the cardioids of the present invention, western blots were utilized to study the isoforms of tropomyosin, SERCA, and cardiac troponin T. Western blots of fetal heart, neonatal heart, cardioids, adult heart, slow skeletal muscle (soleus), and fast skeletal muscle (extensor digitorum longus—EDL) were performed (FIGS. 6A-6C). Samples were homogenized in 9 volumes of ice-cold buffer containing 10 mM $MgCl_2$, 10 mM $KH_2PO_4$, 1 mM EDTA, 5 mM EGTA and freshly added 50 mM β-glycerophosphate, 2.5 mM PMSF, 10 μg/ml leupeptin hemisulfate, 10 μg/ml aprotinin, and 1 mM sodium orthovanadate. Aliquots of homogenate were solubilized in Laemmli sample buffer, subjected to SDS-polyacrylamide gel electrophoresis and electrophoretically transferred to nitrocellulose. Membranes were blocked overnight at 4° C. with 5% non-fat dry milk in tris buffered saline containing 0.1% Tween. The blots were probed with primary antibodies for 1 hour at room temperature followed by incubation with the appropriate horseradish peroxidase conjugated anti-IgG antibody. Antibody-bound protein was detected using West Dura chemiluminescence and a BioRad chemidoc system.

With reference to FIGS. 6A-6C, the cardioids were found to be phenotypically similar to early developmental cardiac muscle. At 4 days after formation, cardioids express both α and β-tropomyosin (Tm), as shown in FIG. 6B wherein mouse monoclonal antibody directed against tropomyosin was recognized by the α and β form of tropomyosin, α expressed in heart and β predominantly in skeletal muscle. Muthuchamy et al. (*Mol Cell Biol* 13, 3311-23, June 1993) have previously shown that at the earliest developmental state of mouse cardiac tissue, both α and β-tropomyosin are expressed, consistent with what is observed in cardioids. The expression of cardiac troponin T (cTnT) followed a similar pattern. As shown in FIG. 6A, goat polyclonal antibody directed against cTnT recognized 3 primary bands in the cardiac tissue that were very low or absent from the skeletal muscles. The fastest migrating band at ~23 kDa was present only in the cardioids, embryonic day 15 (E15) hearts, and neonatal hearts and was inversely related to the developmental state of the tissue. While the fastest migrating isoform decreases with development, the intensity of the ~40 kDa band increased with maturation. There is little of this isoform in the E15 hearts or the cardioids, more in the neonates, and in the adult this isoform accounts for approximately half of the cTnT immunoreactive species. The ~40 kDa isoform observed here is likely the 41 kDa protein observed by Saggin et al. (*J Biol Chem* 263, 18488-92, December 1988) in the adult heart, while the slower migrating form is the 42.5 kDa isoform identified in the developing heart. The 23 kDa protein may represent an early developmental isoform that has yet to be identified in rat. In support of the proposed presence of more cTnT isoforms in fetal rats, five isoforms of cTnT have been developed in the developing rabbit heart (see Gao et al., *J Mol Cell Cardiol* 27, 541-50, January 1995; Anderson and Oakley, *Circ Res* 65, 1087-93, October 1989).

Referring to FIG. 6C, goat polyclonal antibody directed at SERCA recognized a single band with a molecular weight of ~100 kDa in all of the heart tissues and slow skeletal muscle. As expected, SERCA was absent from the fast skeletal muscle sample. The levels of the cardiac/slow skeletal SERCA also suggest that the cardioids are at a very early developmental state. The levels of SERCA are low in the E15 heart, increase by the neonatal state, and are high in both the adult heart and the slow skeletal muscle. The cardioids produce a very low, but detectable, level of SERCA. This is consistent with the work of Liu et al. (*Life Sci* 71, 1279-92, August 2002) that demonstrated SERCA was barely detectable in 9.5 days post-coital (d.p.c.) mouse hearts. SERCA increased 10-fold by 18 d.p.c. and a further 2-fold in the adult. Together, these data strongly suggest that the cardioids have a very early embryonic phenotype, equivalent to 8-9 d.p.c. in the mouse.

Cardioids according to the present invention have been observed to undergo further development during in vivo implantation in isogeneic rats. A fully-formed cardioid is secured to a sterilized acrylic frame, the cardioid-frame combination is placed in a subcutaneous pocket developed in an anesthetized rat and secured to the underlying muscular fascia, and the incision is closed with sutures. The cardioids have been maintained in vivo in this manner for three weeks, and remain stable without becoming absorbed or fibrotic. The cardioids become well vascularized while in vivo and their length is maintained in vivo by the frame, which may actually enhance development. The cardioids are surgically recoverable, are electrically excitable, demonstrate length-tension, force-voltage, and force-frequency relationships, and have a contractile response which can be modulated chemically with β receptor agonists and calcium. The implanted cardioids exhibit automaticity while in vivo and ex vivo. In fact, the degree of automaticity appears to be enhanced by implantation. The amount of force production also appears to be improved by implantation, from about 100 μN in vitro to about 1000 μN in vivo. In an alternative implantation method, cardiac myocytes can be suspended in a fibrin gel supported in a silicone chamber which is implanted in the groin area of an animal.

In summary, the system and method according to the present invention promote the formation of self-organizing, three-dimensional contractile cardioids from disaggregated neonatal rat cardiac cells without exogenous scaffolding or the application of external mechanical strain. The system and method described herein promote the formation of a cohesive monolayer of cardiac cells on a substrate material, then induce the progressive release of the monolayer from the substrate while maintaining adhesion to anchor points within the culture dish. The cardioids self-assemble into papillary-type structures that spontaneously contract, contract in response to electrical stimulation, generate force, and respond to calcium and β-adrenergic stimulation. Cardioids display an early embryonic phenotype, expressing developmental isoforms of several proteins.

The finding that cardioids developed from neonatal cardiac myocytes have an early embryonic phenotype suggests that these cells regenerate in the mode of other tissues. Skeletal muscle, tendon, and other tissues with regenerative capacity respond to injury by recapitulating the developmental program. In the case of skeletal muscle, a repair process that utilizes the developmental isoforms of many of the contractile and regulatory proteins follow injury. Since, like cardiac muscle, skeletal muscle is post-mitotic, this process requires a specialized population of mesenchymal stem cells. The regenerative capacity of neonatal cardiac myocytes suggests that a population of mitotic cardiac myocytes may be present in the heart at this stage and contribute to the formation of the cardioids.

The cardioids according to the present invention will be useful in basic cardiovascular research as a model of tissue development and repair, as well as a model to guide tissue replacement therapy research. Using the cardioids, the role of specific growth factors, gene therapy, or mechanical forces in cardiac muscle development can be studied in isolation, eliminating the confounding variables present in vivo. The ability to generate contractile function and excitability data as shown herein demonstrates the ability of the cardioids of the present invention to be used as an in vitro model of cardiac muscle. These data also suggest that the cardioids of the present invention may be useful in evaluating the effects of pharmaceutical agents on cardiac muscle function. The cardioids could additionally be utilized in genomic and proteomic screens for genes/proteins important in assembly, adhesion, communication during formation, as well as proteomic screens of proteins that are post-translationally modified by any stimuli.

Potential uses for the cardioids of the present invention also include engineering hybrid constructs wherein skeletal muscle constructs are formed by incorporating a percentage of cardiac muscle cells to increase endurance, or wherein cardioids are formed by incorporating a percentage of skeletal muscle cells to increase force production. Tissue engineered ventricles could also be produced by wrapping acellularized aortas with a layer of neonatal cardiac myocytes, thereby resulting in a functional ventricle with the lumen of the aorta simulating a cardiac chamber.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A system for forming a cardiac muscle construct, comprising: cardiac cells cultured in vitro on a substrate to form a cardiac muscle construct without an exogenous scaffold material in a contractile region thereof, wherein at least some of the cells are in contact with and attached to at least two anchors secured to the substrate in a spaced relationship, said cells form a confluent monolayer between the anchors and detach from the substrate to form a self-organizing three-dimensional cardiac muscle construct.

2. The system according to claim 1, wherein the cardiac cells include cardiac myocytes.

3. The system according to claim 1, wherein the cardiac cells include fibroblasts.

4. The system according to claim 1, wherein the cardiac muscle construct is spontaneously contractile.

5. The system according to claim 1, wherein the cardiac muscle construct is responsive to electrical stimuli.

6. The system according to claim 1, wherein the cardiac muscle construct is responsive to chemical stimuli.

7. The system according to claim 1, wherein the cardiac muscle construct is resistant to fatigue.

8. The system according to claim 1, wherein the anchors include silk suture segments coated with cell adhesion molecules.

9. The system according to claim 8, wherein the cell adhesion molecules include laminin.

10. The system according to claim 1, wherein the substrate is coated with cell adhesion molecules.

11. The system according to claim 9, wherein the cell adhesion molecules include laminin.

12. The system according to claim 11, wherein the concentration of laminin is about 0.4 to 2.0 #g/cm2.

13. The system according to claim 1, wherein the cardiac muscle construct is substantially cylindrical.

14. The system according to claim 1, further comprising skeletal muscle cells cultured in combination with the cardiac cells.

15. A method for forming a cardiac muscle construct, comprising: culturing cardiac cells in vitro on a substrate to form a cardiac muscle construct without an exogenous scaffold material in a contractile region thereof, wherein at least some of the cells are in contact with and attached to at least two anchors secured to the substrate in a spaced relationship said cells form a confluent monolayer between the anchors and detach from the substrate to form a self-organizing three-dimensional cardiac muscle construct.

16. The method according to claim 15, wherein providing cardiac cells includes providing cardiac myocytes.

17. The method according to claim 15, wherein providing cardiac cells includes providing fibroblasts.

18. The method according to claim 15, further comprising eliciting a response of the cardiac muscle construct to electrical stimuli.

19. The system according to claim 15, further comprising eliciting a response of the cardiac muscle construct to chemical stimuli.

20. The method according to claim 15, wherein the anchors include silk suture segments coated with cell adhesion molecules.

21. The method according to claim 20, wherein the cell adhesion molecules include laminin.

22. The method according to claim 15, further comprising coating the substrate with cell adhesion molecules.

23. The method according to claim 22, wherein the cell adhesion molecules include laminin.

24. The method according to claim 23, wherein the concentration of laminin is about 0.4 to 2.0/~g/cm2.

25. The method according to claim 15, further comprising the step of measuring a passive or active force of the cardiac muscle construct and then using the measured force to control the further formation of the cardiac muscle construct.

26. The method according to claim 15, further comprising culturing skeletal muscle cells in combination with the cardiac cells.

27. A cardiac muscle construct, comprising: cardiac myocytes provided on a substrate to form a cardiac muscle construct without an exogenous scaffold material in a contractile region thereof, wherein at least some of the myocytes are in contact with and attach to at least two anchors secured to the substrate in spaced relationship, said cardiac myocytes are cultured in vitro to form a confluent monolayer between the anchors, and detach from the substrate to form a self-organizing three-dimensional cardiac muscle construct.

28. The cardiac muscle construct according to claim 27, further comprising fibroblasts provided in combination with the cardiac myocytes.

29. The cardiac muscle construct according to claim 27, wherein the construct is spontaneously contractile.

30. The cardiac muscle construct according to claim 27, wherein the construct is responsive to electrical stimuli.

31. The cardiac muscle construct according to claim 27, wherein the construct is responsive to chemical stimuli.

32. The cardiac muscle construct according to claim 27, wherein the construct is resistant to fatigue.

33. The cardiac muscle construct according to claim 27, wherein the construct includes adherens junctions formed between the cardiac myocytes.

34. The cardiac muscle construct according to claim 27, wherein the construct includes gap junctions between the cardiac myocytes.

35. The cardiac muscle construct according to claim 27, wherein the cardiac muscle construct is substantially cylindrical.

* * * * *

UNITED STATES PATENT AND TRADEMARK OFFICE
CERTIFICATE OF CORRECTION

PATENT NO.       : 7,338,798 B2                                    Page 1 of 1
APPLICATION NO. : 10/663577
DATED            : March 4, 2008
INVENTOR(S)      : Robert G. Dennis et al.

It is certified that error appears in the above-identified patent and that said Letters Patent is hereby corrected as shown below:

Column 12, Line 10, Claim 11:

Delete "9" and insert -- 10 --.

Column 12, Line 35, Claim 19:

Delete "system" and insert -- method --.

Signed and Sealed this

Tenth Day of June, 2008

JON W. DUDAS
*Director of the United States Patent and Trademark Office*